(12) United States Patent
Zhang

(10) Patent No.: US 11,666,596 B2
(45) Date of Patent: Jun. 6, 2023

(54) NUCLEOTIDE, POLYPEPTIDE AND APPLICATIONS THEREOF

(71) Applicant: THE FIRST AFFILIATED HOSPITAL, SUN YAT-SEN UNIVERSITY, Guangdong (CN)

(72) Inventor: Nu Zhang, Guangdong (CN)

(73) Assignee: THE FIRST AFFILIATED HOSPITAL, SUN YAT-SEN UNIVERSITY, Guangdong (CN)

( * ) Notice: Subject to any disclaimer, the term of this patent is extended or adjusted under 35 U.S.C. 154(b) by 670 days.

(21) Appl. No.: 16/620,158

(22) PCT Filed: Jun. 8, 2018

(86) PCT No.: PCT/CN2018/090519
§ 371 (c)(1),
(2) Date: Dec. 6, 2019

(87) PCT Pub. No.: WO2018/224043
PCT Pub. Date: Dec. 13, 2018

(65) Prior Publication Data
US 2020/0179433 A1    Jun. 11, 2020

(30) Foreign Application Priority Data

Jun. 8, 2017 (CN) .......................... 201710431301.3

(51) Int. Cl.
| | | |
|---|---|---|
| A61K 38/00 | (2006.01) | |
| A61K 31/713 | (2006.01) | |
| C07K 14/47 | (2006.01) | |
| C12N 9/14 | (2006.01) | |
| G01N 33/574 | (2006.01) | |

(52) U.S. Cl.
CPC ............ *A61K 31/713* (2013.01); *C07K 14/47* (2013.01); *C12N 9/14* (2013.01); *G01N 33/57407* (2013.01); *G01N 33/57496* (2013.01); *A61K 38/00* (2013.01); *G01N 2333/916* (2013.01)

(58) Field of Classification Search
CPC ..... A61P 35/00; C12Q 1/6886; G01N 33/574; G01N 2800/28
See application file for complete search history.

(56) References Cited

U.S. PATENT DOCUMENTS

2015/0159161 A1* 6/2015 Krieg ..................... C07H 21/02
435/375

FOREIGN PATENT DOCUMENTS

| CN | 101988091 A | 3/2011 |
|---|---|---|
| CN | 103642931 A | 3/2014 |
| CN | 104178488 A | 12/2014 |
| WO | 2010065787 A2 | 6/2010 |
| WO | 2011103339 A1 | 8/2011 |

OTHER PUBLICATIONS

Deloukas et al, Nature 429:375-381, 2004.*
International Search Report of PCT Application PCT/CN2018/090519, dated Sep. 8, 2018.
NM_000314.6., "*Homo sapiens* phosphatase and tensin homolog (PTEN), transcript variant 1, mRNA", GenBank, pp. 1-14, May 7, 2017 (see "Comment", "Features" and "Origin").
NM_001304718.1, "*Homo sapiens* phosphatase and tensin homolog (PTEN), transcript variant 2", GenBank, pp. 1-11, Apr. 7, 2017 (see "Comment", "Features" and "Origin").
Tzani, et al., "Systematic analysis of the PTEN 5' leader indentifies a major AUU initiated proteoform", Open Biology, vol. 6:150203; pp. 1-13, May 25, 2016.
Han et al., "Regulation of constitutive expression of mouse PTEN by the 5'—untranslated region", Oncogene, vol. 22, pp. 5325-5337, Dec. 31, 2003.
First Office Action of corresponding CN application (CN109022462A) dated May 17, 2021.

* cited by examiner

*Primary Examiner* — Mark Halvorson
(74) *Attorney, Agent, or Firm* — Pearne & Gordon LLP

(57) ABSTRACT

Provided are applications of an upstream Open Reading Frame (uORF) of a Phosphatase and Tensin homolog (PTEN) gene and a polypeptide coded by the same. A potential ORF of 96 bases (31aa-uORF) existing in the 5' UTR of the PTEN can code an oligopeptide of 31 amino acids (named PTEN-31aa) and plays an important role in the development and progression process of tumors. Provided is a new diagnostic and therapeutic method and a drug screening platform for PTEN expression regulation related diseases, in particular gliomas. Also provided is a polypeptide for treatment of PTEN expression regulation related diseases.

3 Claims, 5 Drawing Sheets
Specification includes a Sequence Listing.

NUCLEOTIDE, POLYPEPTIDE AND APPLICATIONS THEREOF

BACKGROUND OF THE INVENTION

Technical Field

The present invention belongs to the field of bio-medicine and particularly relates to applications of an upstream Open Reading Frame (uORF) of a Phosphatase and Tensin homolog (PTEN) gene and a protein coded by the same.

Background Art

Gliomas are tumors that stem from the brain, which generally result from pathological changes of glial cells, and are the most common malignant tumors in human's central nervous system. The WHO has classified the gliomas into grade I to grade IV according to clinicopathological evaluation of tumors, among which grade I fibrous astrocytomas exhibit the lightest symptoms and grade IV glioblastoma multiforme exhibit symptoms at the highest grade of malignancy, which is the most common, most extensively used grade (Louis et al., 2007). CBTRUS statistics show that the malignant gliomas take a proportion of up to 70% in primary malignant brain tumors and their incidence is about 5 per 100,000 people. The clinical cure rate of the malignant gliomas is extremely low and the five-year survival rate is only higher than that of the pancreatic cancer and the lung cancer. In the United States, there are about 10,000 patients suffering from malignant gliomas under treatment every year. About half of the patients can live for one year, and only one quarter of them can live for two years. With the advent of new treatment means in recent years, the survival time of patients is obviously prolonged (Nakazato et al., 2008). Therefore, new therapeutic regimens having better curative effect can be ultimately found out only if the research on the pathogenesis of the malignant gliomas is enhanced and the pathogenesis of the malignant gliomas is comprehensively known.

The pathogenesis of the malignant gliomas is very complex and not yet clear at present. However, research has shown that the Inherited genetic abnormalities such as NF (neurofibromatosis type I and type II) and TSC (tuberous sclerosis complex) gene mutation could stimulate the progression of the malignant gliomas (Reuss et al., 2009). Of course, the abnormal expression of many different cancer genes is also related to the progression of the malignant gliomas (Rader et al., 1993). Genetic polymorphisms of DNA repair genes ERCC1, ERCC2 and XRCC1, can increase the glioma risk. That is to say, the change or deletion of DNA repair mechanism can promote the generation of gliomas (Adel et al., 2014). The most common mutations in gliomas occur in isocitrate dehydrogenase I and II (IDH1 and IDH2) genes, and up to 80% of low risk gliomas and moderate malignant gliomas have the same mutation in the IDH1 gene (Cohen et al., 2013). A study on long-term sampling results of 51 glioma patients showed that the IDH1 gene mutation was a mutation that could be detected at very early time, which occurred before the P53 gene mutation and the loss of heterozygosity of chromosome 1p/19q, so the IDH1 mutation was the earliest help for mutation (Watanabe et al., 2009). In addition to IDH1 and IDH2, there are many other gene mutations in the development and progression process of malignant gliomas. For example, 1) EGFR (epidermal growth factor receptor) amplification or rearrangement that is rare in other tumors takes a high proportion in gliomas (Zadeh et al., 2013); 2) P53 gene mutation, which is common in most tumors, occurred at high rate in various types of gliomas (for example, the proportion of its presence in low-malignancy astrocytic tumours reaches up to 60%) (Zheng et al., 2008); 3) the PTEN (phosphatase and tensin homolog) mutation accounts for about 30% in primary glioblastomas (Zheng et al). 2008); and 4) the probabilities of the presence of the loss of heterozygosity of chromosome 1p/19q are different, in different types of gliomas. In oligodendroblastomas, it presents at a rate of up to 90%, while in diffuse astrocytomas, it presents at a rate of only 15% (Ducray et al., 2009). Although many studies have involved the pathogenesis of the malignant gliomas, the exact molecular mechanism is still unknown and worth deeply exploring so as to provide better guidance for clinical treatment.

The coding gene PTEN of the Phosphatase and Tensin homolog (PTEN) is located on the chromosome 10q23.3, which is one of the most common genes that are down-regulated because of deletion or mutation in various human tumors (such as brain cancer, breast cancer, prostate cancer) (Li et al., 1997). As a tumor suppressor gene, the PTEN plays an important role in regulating cell growth, invasion, apoptosis, DNA damage repair and tumor cell resistance to chemoradiotherapy (Dean et al., 2005; Koul, 2008; Mellinghoff et al., 2005; Ming and He, 2012; Ortega-Molina and Serrano, 2013). The deletion of PTEN expression is considered as an early event in the progression of the gliomas, and PTEN mutation occurs in 60% of GBM (glioblastoma), which is the most common gene change (Bianco et al., 2003; Srividya et al., 2011). The PTEN mainly functions as a negative regulation factor for PI3K/Akt pathway. In contrast to PI3K, the PTEN takes effects to transform PIP3 into PI-4,5-P2 by dephosphorylation and to suppress all downstream signaling pathways regulated by Akt by reducing the activation of the Akt (Trotman et al., 2006). Previous studies have shown that in gliomas, the activation of the PI3K/Akt pathway directly affects the malignancy of the gliomas and plays a key role in the development and progression process of GBMs (Rodriguez et al., 2011; Sonoda et al., 2001). Although previous studies have shown that the tumor suppressor gene PTEN plays an important regulatory role in gliomas, the exact mechanism thereof is still unclear. Therefore, it is of great significance for revealing the development and progression of the gliomas according to discover all the active variants of the PTEN in the gliomas and explore the tumor suppression mechanism thereof.

At present, the standard treatment regimen for the gliomas is standardized diagnosis and treatment, relying mainly on surgical treatment. The principle of the surgical treatment is to maximize the resection of tumors under the principle of protecting the normal brain tissue around the tumor as far as possible, in order to achieve the purposes of reducing the probability of postoperative recurrence and metastasis of patients and greatly improving the survival rate and quality of life of the patients. Of course, in addition to the surgical treatment, the treatment of the gliomas in combination with multidisciplinary approaches, especially supplementary means such as chemotherapy, immunization and Chinese medicine, has attracted more and more attention. At present, the first-line clinical drug for chemotherapy for the gliomas is Temozolomid (TMZ). The specific principle is that TMZ is transformed into active compound MTIC by rapid non-enzymatic catalysis under the physiological PH condition and the MTIC can alkylate the 06 and N2 sites of guanine to play the cytotoxic effect. However, the sensitivity of patients to the TMZ depends on the expression quantity of MGMT methyltransferase with a negative correlation therebetween, thus limiting the wide application of the TMZ in clinical practice. Immunotherapy for the gliomas can be done from the following aspects: immunosuppression of the gliomas (for example, antibodies against CDLA-4 protein can increase the survival rate of glioma model mice, and many other antibodies targeted against immunomodulatory protein are in clinical trials), and glioma vaccines (in clinical trials, for example, ATL-D vaccine was used to treat glioma patients, and 28 out of 32 subjects exhibited immune response, indicating great improvement in clinical treatment effect). The treatment of the gliomas by traditional Chinese medicine is still at the stage of whole treatment. That is, the balance between Yin and Yang, Qi and blood, and Zang-Fu functions of the organism is regulated so as to control the progression and metastasis of the gliomas, reduce recurrence and improve the survival time and the quality of life of patients on overall level. In addition, some Chinese herbal compound monomers showed good antiglioma activity in preclinical cell experiments. However, if the quality standardization, safety and toxicity problems of the traditional Chinese medicine are not solved, the application of the traditional Chinese medicine to clinical treatment will be greatly limited.

Upstream open reading frames (uORF) are open reading frames located in the mRNA 5' untranslated region. The uORF can regulate eukaryotic gene expression (Lovett et al., 1996). In general, the translation of the uORFs will inhibit the expression of their respective maternal genes (Vilela et al., 2003). In bacteria, the uORFs are also called leader peptides, which were first discovered in research on regulation of genes involved in amino acid synthesis or metastasis (Lovett et al., 1996). With the deepening of sequencing precision and the improvement of 5'UTR sequence database (Pesole et al., 1999), tens of thousands of uORFs can be predicted through some algorithms. In theory, the uORFs can be present in the upstream of any mRNA (McCarthy et al., 1998; Vilela et, 1998), of course, their confirmation and specific functions still need to be verified by many biological experiments. In general, the uORFs in a variety of organisms are mainly involved in the regulation of some key cellular biological processes (Vilela et al., 2003). The uORFs discovered or proved at present are generally present in the upstream of some genes regulating the key cytological process and involved in the regulation of the expression of genes corresponding to downstream maternal mRNAs, for example, G1 cell cycle protein CLN3 regulating cell cycle in *Saccharomyces cerevisiae* (Polymenis et al., 1997), apoptosis regulation BCL2 in human (Harigai et al., 1996), important cancer gene MDM-2 in human (Brown et, 1999), Moloney sarcoma gene c-mos in mice (1997) (Steel et al., 1997). These findings suggest that functional uORFs are usually involved in the regulation of the vital physiological processes such as cell growth and apoptosis and different uORFs play different roles in different species or physiological processes (McCarthy et al., 1998; Vilela et al., 1998; Vilela et al., 1999). Although a lot of uORFs have been found in organisms with relatively simple research background, such as *Saccharomyces cerevisiae* and fungi, there are more unknown uORFs waiting for us to study and discover with the development of experimental means and analytical methods. Moreover, more and more uORFs will be discovered and their physiological functions will be determined. These uORFs may have more complicated regulation modes waiting for us to discover in addition to this CIS regulation effect.

Recently, two research groups published articles on Cell metabolism and Science, both demonstrating that there are new transcriptional starting sites in the 5'UTR of the PTEN gene to each code new spliceosomes of the PTEN, which are named PTEN-A and PTEN-long, respectively. The PTEN-A, published on Cell metabolism, has been proved to be involved in regulating mitochondrial respiration to regulate cell metabolism. The PTEN-long, published on Science, can be secreted out of cells and taken by other cells to regulate cell survival and promote tumor cell death (Liang et al., 2014; Hopkins et al., 2013). The research of the two groups on PTEN's new ORFs provides us with new research inspiration. Because the 5'UTR of the PTEN is long and has about 1000 bp nucleotides, we may think about whether there are other transcriptional starting sites in the upstream of the PTEN, or there is a new small ORF? Looking up the literature, it was found that the research of Han et al. in 2000 showed that if the 5'UTR of mouse's PTEN is transferred into tumor cells, the cell cycle would be arrested so that the growth of the tumor cells could be inhibited. The Han team considered this was because of different activities of promoters due to different lengths of the 5'UTR regions (Han et al., 2013).

BRIEF SUMMARY OF THE INVENTION

According to the present invention, there is found an open reading frame of 96 bases in the 5'UTR region of human PTEN gene (NCBI No.: NM 000314), which is named 31aa-uORF and can code an oligopeptide of 31 amino acids that is named PTEN-31aa (FIG. 1). The molecular weight of this oligopeptide is approximately 4-5 KD. The 31aa-uORF has the nucleotide sequence of SEQ ID NO: 1. The PTEN-31aa has the amino acid sequence of SEQ ID NO: 2.

In some embodiments, the present disclosure relates to nucleic acid molecules encoding PTEN-31aa molecules. The present disclosure provides, for example, nucleic acid molecules encoding the sequence of SEQ ID NO: 2, and provides nucleic acid molecules encoding variants, and modified forms, of SEQ ID NO: 2.

In other embodiments, the present disclosure relates to PTEN-31aa molecules. The present disclosure provides, for example, polypeptides comprising, consisting essentially of, or consisting of, the sequence of SEQ ID NO: 2; and provides variants, and modified forms, of polypeptides comprising, consisting essentially of, or consisting of, the sequence of SEQ ID NO: 2.

In further embodiments, antibodies that specifically bind to PTEN-31aa molecules are provided, as are nucleic acid probes that specifically bind to 31aa-uORF sequences.

In some embodiments, the present disclosure relates to methods for treating diseases. The present disclosure provides, for example, methods for treating tumors, such as PTEN regulated-related tumors. The present disclosure provides, for example, methods of treating tumors through administering nucleic acid molecules encoding PTEN-31aa molecules, and/or administering PTEN-31aa molecules.

The present disclosure further relates to detecting and/or determining whether a tumor is a PTEN-regulated tumor. In some embodiments, where a tumor in a subject, or a tumor sample from a subject, is detected and/or determined to be a PTEN-regulated tumor, the subject is treated with a nucleic acid encoding a PTEN-31aa molecule, and/or is treated with a PTEN-31aa peptide molecules.

DETAILED DESCRIPTION OF THE INVENTION

Figure 1:
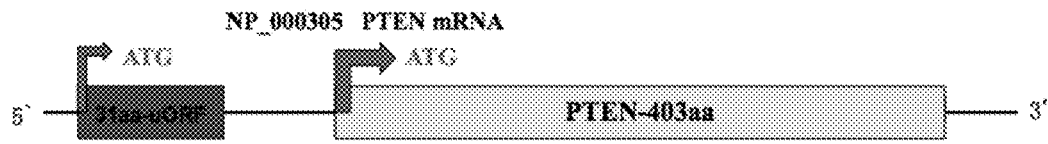
FIG. 1 illustrates a location diagram of 31aa-uORF in PTEN mRNA.

In some embodiments, the present disclosure relates to nucleic acid molecules encoding PTEN-31aa molecules. The present disclosure provides, for example, nucleic acid molecules encoding the sequence of SEQ ID NO: 2, and provides nucleic acid molecules encoding variants, and modified forms, of SEQ ID NO: 2. In one embodiment, the nucleic acid is a 31aa-uORF having the nucleotide sequence of SEQ ID NO: 1.

In some embodiments, the 31aa-uORF is a nucleic acid that is at least 90%, at least 91%, at least 92%, at least 93%, at least 94%, at least 95%, at least 96%, at least 97%, at least 98%, or at least 99% identical to any of the nucleic acids set forth as SEQ ID NO: 1.

In some embodiments, the nucleic acid encoding the PTEN-31aa molecule is a nucleic acid that has the sequence of SEQ ID NO: 1 except that it contains at least one substitution, addition, and/or deletion modification. It may contain, for example, at least 1, at least 2, at least 3, at least 4, at least 5, at least 10, at least 15, at least 25, or at least 50, substitution, addition, and/or deletion modifications.

In some embodiments, the nucleic acid encoding the PTEN-31aa molecule consists of, or consists essentially of, the sequence of SEQ ID NO: 1.

In certain embodiments, a nucleic acid sequence encoding the PTEN-31aa molecule is present within a vector. In some embodiments, the vector may be configured for in vitro or in vivo expression of the nucleic acid sequence encoding the PTEN-31aa molecule. The vector may contain, for example, one or more sequences that are heterologous to the nucleic acid sequence encoding the PTEN-31aa molecule, such as, for example, sequences encoding a selectable marker (such as a drug resistance gene, a fluorescent protein gene, a lacZ gene, and the like). Such vectors may also contain one or more expression control sequences, such as promoter and enhancer sequences, an IRES sequence, a polyadenylation sequence, and/or a termination sequence, for example. The promoter may be, for example, a tissue- or cell-specific promoter, and/or be an inducible or a constitutive promoter.

In some embodiments, the nucleic acid encoding the PTEN-31aa molecule is a nucleic acid that has the sequence of SEQ ID NO: 1 except that it contains at least one substitution, addition, and/or deletion modification. It may contain, for example, at least 1, at least 2, at least 3, at least 4, at least 5, at least 10, at least 15, at least 25, or at least 50, substitution, addition, and/or deletion modifications.

In some embodiments, the PTEN-31aa is a amino acid that is at least 90%, at least 91%, at least 92%, at least 93%, at least 94%, at least 95%, at least 96%, at least 97%, at least 98%, or at least 99% identical to any of the amino acids set forth as SEQ ID NO: 2.

In one aspect, the present invention provides a nucleic acid fragment 31aa-uORF or a polypeptide PTEN-31aa coded by the same.

In some embodiments, the PTEN-31aa molecule has the sequence of SEQ ID NO: 2 except that it contains at least one substitution, addition, and/or deletion modification. It may contain, for example, at least 1, at least 2, at least 3, at least 4, at least 5, at least 10, or at least 15 substitution, addition, and/or deletion modifications.

Comparisons of the 31aa-uORF coded micropeptide of human with sequences of other species revealed homologs in other species, including mouse, pig, cow, and rabbit (SEQ ID NOs: 6-9). The comparisons suggest that the first 15 amino acids of the 31aa-uORF coded micropeptide and homologs correspond to a conserved region, with a consensus sequence of MWRDSLCX1AAGYX2X3G (SEQ ID NO: 10), wherein: X1 corresponds to A or T; X2 corresponds to A or P; and X3 corresponds to L, F, or P.

In another aspect, the present invention provides application of an upstream open reading frame 31aa-uORF nucleotide sequence of the PTEN gene or a nucleotide sequence for coding an equal amino acid sequence with the same or a polypeptide PTEN-31aa coded by the same in preparing drugs for treating or preventing tumors.

In another aspect, the present invention also provides application of a detection reagent for 31aa-uORF or a polypeptide PTEN-31aa coded by the same in preparing a reagent for tumor diagnosis and/or prognosis. Preferably, the reagent for tumor diagnosis and/or prognosis comprises: a probe for detecting the 31aa-uORF, or a primer for amplifying the 31aa-uORF, or an anti-body against the PTEN-31aa.

In some embodiments, PTEN-31aa molecules are detectable with an antibody. The antibody may be a monoclonal antibody, a polyclonal antibody, a multivalent antibody, a multispecific antibody (e.g., bispecific antibody), and/or an antibody fragment that specifically binds to a PTEN-31aa molecule. The antibody may be a chimeric antibody, a humanized antibody, a CDR-grafted antibody, or a human antibody, for example. The antibody fragment may be, for example, a Fab, Fab', F(ab')2, Fv, Fd, single chain Fv (scFv), disulfide bond Fv (sdFv), or a VL or a VH domain. The antibody may be in the form of a conjugate, for example, conjugated to a tag, a detectable label, or a cytotoxic agent. The antibody may be of the isotype IgG (e.g., IgG1, IgG2, IgG3 or IgG4), IgA, IgM, IgE or IgD).

In another aspect, the present invention also provides a pharmaceutical composition for tumor treatment or prevention. The pharmaceutical composition contains a 31aa-uORF nucleotide sequence of the PTEN gene, or a nucleotide sequence for coding an equal amino acid sequence with the same, or a polypeptide PTEN-31aa coded by the same. Optionally, the pharmaceutical composition may also comprise one or more pharmaceutical excipients, or pharmaceutical carriers such as lentivirus and the like.

The present disclosure also relates to methods for treating tumors. The tumor may be a solid tumor or a blood tumor, and may be a tumor in which PTEN regulates the PI3K/Akt pathway. In some embodiments, the tumor may be a tumor in which PTEN is down-regulated, mutated, or deleted, and/or a tumor in which 31aa-uORF is down-regulated, mutated, or deleted.

Preferably, the tumor is brain cancer, liver cancer, colorectal cancer, bladder cancer, breast cancer, cervical cancer, prostate cancer, glioma, melanoma, pancreatic cancer, nasopharyngeal carcinoma, lung cancer, or gastric cancer. In some embodiments, the tumor is brain cancer, breast cancer, or prostate cancer. In certain embodiments, the tumor is neuroglioma.

Compositions containing a nucleic acid sequence encoding a PTEN-31aa molecule, or containing a PTEN-31aa peptide molecule, may be administered once a week, or several times (e.g., 2, 3, 4, 5, 6, 7, 8, 9 or 10) a week. The compositions may be administered for one or several weeks (1, 2, 3, 4, 5, 6, 7, 8, 9, or 10), for a month, or even for several months (2, 3, 4, 5, 6, 7, 8, 9, 10, 11 or 12 or more). In some instances, treatment may be continued for a year or for several years.

In some embodiments, compositions containing a nucleic acid sequence encoding a PTEN-31aa molecule, or containing a PTEN-31aa peptide molecule, are administered in conjunction with additional anti-tumor therapies. For example, the subject may be further treated with a chemotherapeutic drug (such as an alkylating agent, an anti-metabolite, an anti-mitotic, an alkaloid, a taxane, a topoisomerase inhibitor, a cytotoxic antibiotic, or a combination thereof), radiation, or surgery. In some embodiments, the chemotherapeutic agent is selected from carmustine, fotemustine, lomustine and temozolomide. The subject may also be treated with an antibody therapy, such as bevacizumab. The present disclosure also relates to methods for treating tumors. The tumor may be a solid tumor or a blood tumor, and may be a tumor in which PTEN regulates the PI3K/Akt pathway. In some embodiments, the tumor may be a tumor in which PTEN is down-regulated, mutated, or deleted, and/or a tumor in which 31aa-uORF is down-regulated, mutated, or deleted.

Preferably, the tumor is brain cancer, liver cancer, colorectal cancer, bladder cancer, breast cancer, cervical cancer, prostate cancer, glioma, melanoma, pancreatic cancer, nasopharyngeal carcinoma, lung cancer, or gastric cancer. In some embodiments, the tumor is brain cancer, breast cancer, or prostate cancer. In certain embodiments, the tumor is neuroglioma.

Compositions containing a nucleic acid sequence encoding a PTEN-31aa molecule, or containing a PTEN-31aa peptide molecule, may be administered once a week, or several times (e.g., 2, 3, 4, 5, 6, 7, 8, 9 or 10) a week. The compositions may be administered for one or several weeks (1, 2, 3, 4, 5, 6, 7, 8, 9, or 10), for a month, or even for several months (2, 3, 4, 5, 6, 7, 8, 9, 10, 11 or 12 or more). In some instances, treatment may be continued for a year or for several years.

In some embodiments, compositions containing a nucleic acid sequence encoding a PTEN-31aa molecule, or containing a PTEN-31aa peptide molecule, are administered in conjunction with additional anti-tumor therapies. For example, the subject may be further treated with a chemotherapeutic drug (such as an alkylating agent, an anti-metabolite, an anti-mitotic, an alkaloid, a taxane, a topoisomerase inhibitor, a cytotoxic antibiotic, or a combination thereof), radiation, or surgery. In some embodiments, the chemotherapeutic agent is selected from carmustine, fotemustine, lomustine and temozolomide. The subject may also be treated with an antibody therapy, such as bevacizumab.

In another aspect, the present invention also provides a kit for tumor diagnosis and/or prognosis. The kit contains: a probe for detecting the 31aa-uORF, or a primer for amplifying the 31aa-uORF, or an anti-body against PTEN-31aa.

In some embodiments, the expression level (and/or the sequence) of the 31aa-uORF is determined for a tumor from a subject, and compared to that of a control sample. The control sample may be, for example, non-tumor cells, tumor cells in which PTEN is not down-regulated, mutated, or deleted; or tumor cells in which 31aa-uORF expression is known not to be down-regulated, mutated, or deleted. In some embodiments, the control cells are normal brain glial cells. In additional embodiments, subjects specifically determined to have tumors in which PTEN is down-regulated, mutated, or deleted; and/or in which 31aa-uORF expression is down-regulated; mutated, or deleted, are then specifically selected for treatment with one or more treatment methods described herein.

In another aspect, the present invention also provides an expression vector for coding PTEN-31aa and a host cell for expressing the vector as well as uses thereof in tumor suppression/prevention/treatment.

Figure 6:
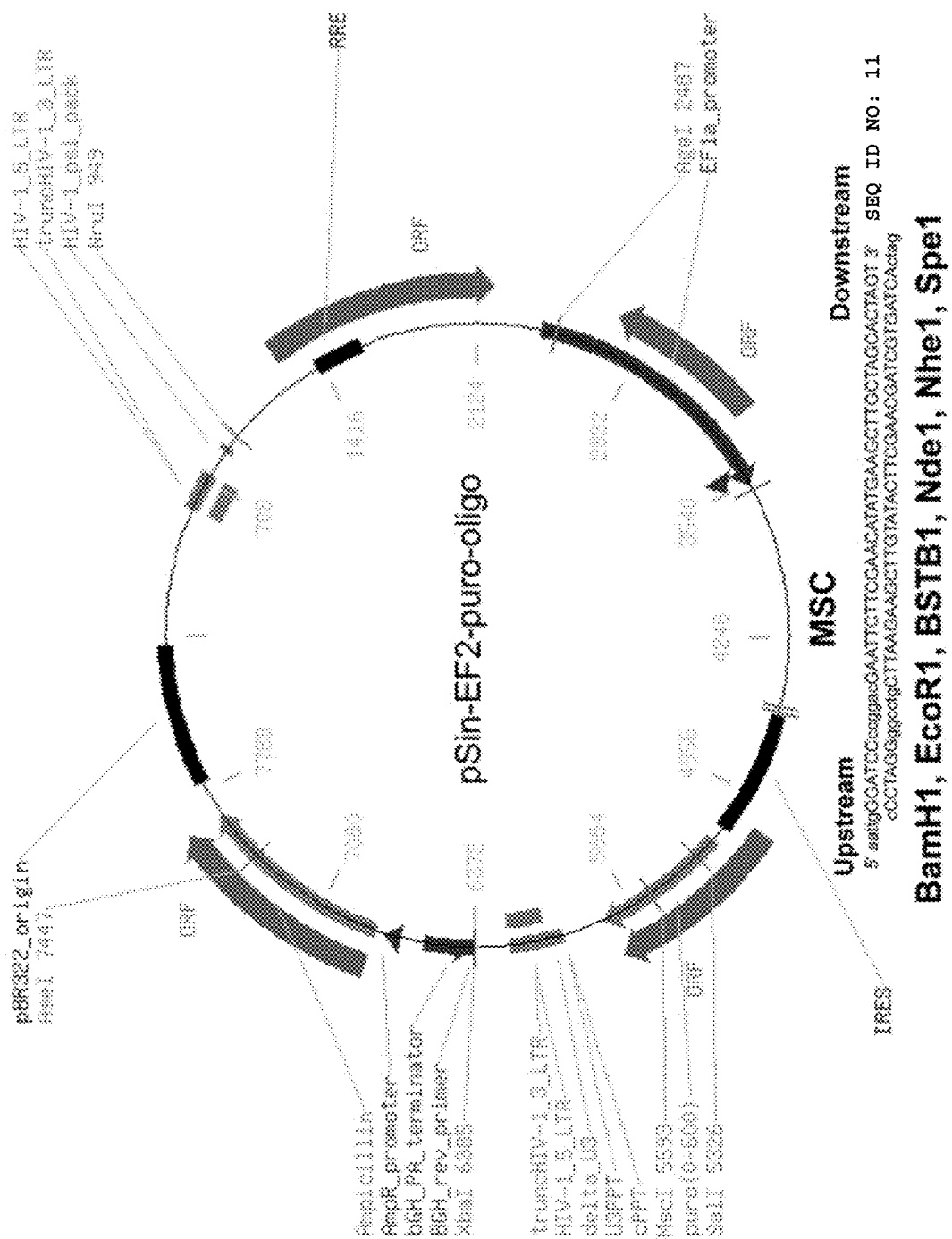
FIG. 6 illustrates the structure of the pSin-E2F-puro-oligo.

Polynucleotides 31aa-uORF of the present invention are inserted into expression vectors (i.e., a nucleic acid construct) to enable expression of the recombinant polypeptide. In one embodiment, the expression vector of the present invention includes additional sequences which render this vector suitable for replication and integration in eukaryotes. In one embodiment, the expression vector of the present invention includes a shuttle vector which renders this vector suitable for replication and integration in eukaryotes. In some embodiments, cloning vectors comprise transcription and translation initiation sequences (e.g., promoters, enhancers) and transcription and translation terminators (e.g., polyadenylation signals). In some embodiments, the vector used in the present invention is p-Sin-E2F-puro-oligo or pCDH-CMV-MCS-EF1-Puro. The structure of the p-Sin-E2F-puro-oligo is showed in FIG. 6.

In another aspect, the present invention also provides a polypeptide synthesized chemically or produced by recombinant expression, which has the amino acid sequence shown by SEQ ID NO: 2, or at least 90%, at least 91%, at least 92%, at least 93%, at least 94%, at least 95%, at least 96%, at least 97%, at least 98%, or at least 99% identical to any of the amino acids set forth as SEQ ID NO: 2. It has been proved by experiments that polypeptides, whether synthesized chemically or produced by recombinant expression, have the function of suppressing tumor. The tumor is PTEN regulation-related tumor. The PTEN regulation is particularly that the PTEN is involved in negative regulation of PI3K/Akt pathway. The tumor is preferably glioma, and more preferably, neuroglioma.

As discussed herein, the tumor is PTEN regulation-related tumor.

Alternatively, the tumor is brain cancer, breast cancer, prostate cancer. More preferably, the tumor is glioma.

The PTEN gene is one of the most common genes that are down-regulated due to deletion or mutation in various human tumors (such as brain cancer, breast cancer, prostate cancer) (Li et al., 1997). As a tumor suppressor gene, the PTEN plays an important role in regulating cell growth, invasion, apoptosis, DNA damage repair and tumor cell resistance to chemoradiotherapy. An up-stream Open Reading Frame (uORF) can regulate expression of a gene downstream thereof. Therefore, it can be inferred that the uORF (31aa-uORF) of the PTEN and the polypeptide (PTEN-31aa) coded by the same in the present invention may play a regulatory role in the PTEN regulation related diseases and thus play a role in tumor suppression.

Therein, the PTEN regulation is particularly that the PTEN is involved in negative regulation of PI3K/Akt pathway. The PTEN can transform PIP3 into PI-4,5-P2 by dephosphorylation and suppress all downstream signaling pathways regulated by Akt by reducing the activation of the Akt (Trotman et al., 2006). In gliomas, the activation of the PI3K/Akt pathway directly affects the grade malignancy of gliomas and plays a key role in the development and progression process of GBMs (Rodriguez et al., 2011; Sonoda et al., 2001). Therefore, the PTEN is considered as an important suppressor for tumors by negatively regulating the Phosphatidylinositol 3-kinase (PI3K) signaling pathway.

Figure 2:
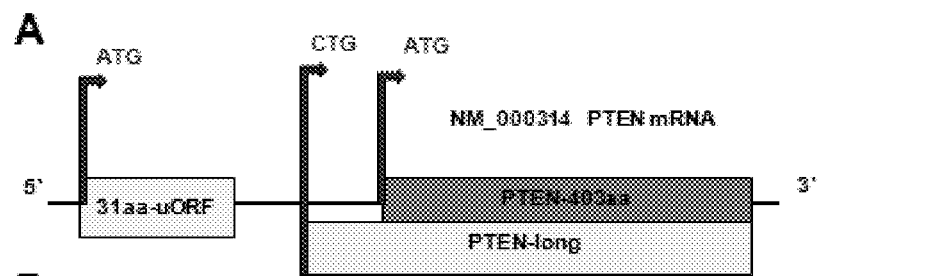
FIG. 2 illustrates prediction and endogenous expression identification of 31aa-uORF coded micropeptide;
  A: diagram of location of 31aa-uORF in PTEN mRNA;
  B: analysis of homology of 31aa-uORF coded micropeptide in different species;
  C: western detection of endogenous expression of 31aa-uORF in cells by specific antibody of 31aa-uORF coded micropeptide.
  D: The expression amount of 31aa-uORF-encoded micropeptides in normal glial cells and different glioma cells.
Figure 2:
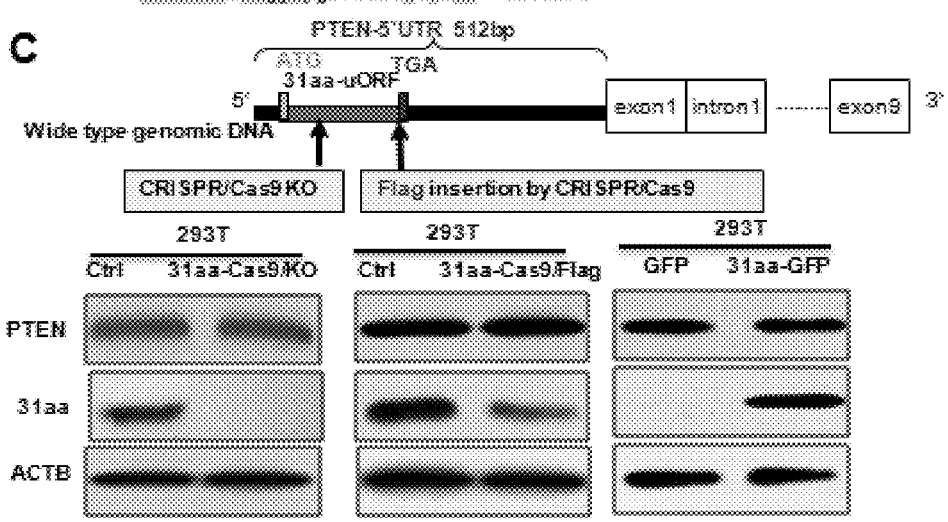
Figure 2:
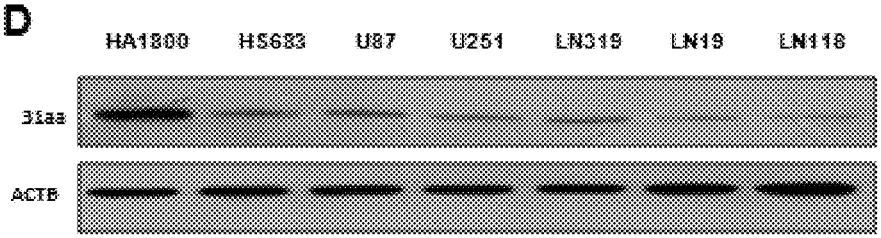

In one aspect, we have detected and identified the uORF coded micropeptide in 293 and U251 cells by preparing a PTEN-31aa specific antibody. Meanwhile, it also has been found that the expression quantity of the micropeptide in normal brain glial cells is much higher than that in glioma cells (FIG. 2).

Figure 3:
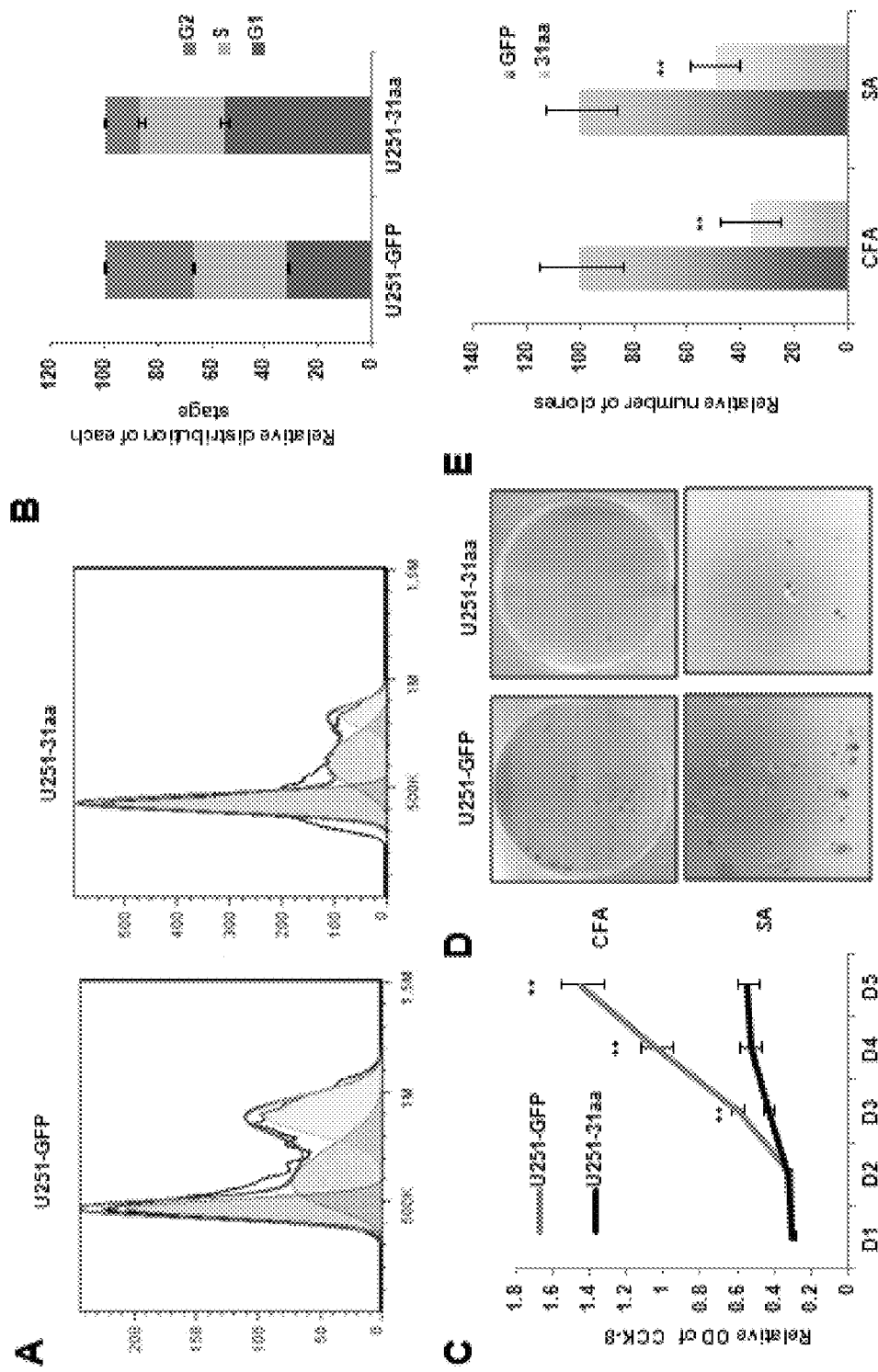
FIG. 3 illustrates that 31aa-uORF plays a role as a cancer suppressor polypeptide in glioma U251 cells;
  A: the cell cycles of U251 cells that over-expressed 31aa-uORF detected by flow cytometry;
  B: the statistical histogram of A, wherein the histogram indicates G2 (DNA postsynthetic phase), S (DNA synthesis phase), G1 (DNA presynthetic stage) sequentially from top to bottom;
  C: measurement of changes of the growth curve by detection of the OD value of the CCK-8;
  D: detection of the colony forming ability of cells by Clone Formation Assay (CFA) and Soft Agar (SA);
  E: quantification of CFA and soft agar.

In one aspect, according to the present invention, an overexpression lentivirus vector is constructed based on the base sequence of the 31aa-uORF; the overexpression lentivirus vector is packaged and then employed to infect U251 glioma cells; and then a glioma cell line of stably overexpressed 31aa-uORF coded micropeptide is obtained by screening, and then verified on cellular biological functions thereof. In the U251 glioma cells, the overexpressed 31aa-uORF coded micropeptide can significantly suppress the growth, proliferation and clone formation of the U251 glioma cells (FIG. 3).

Figure 4:
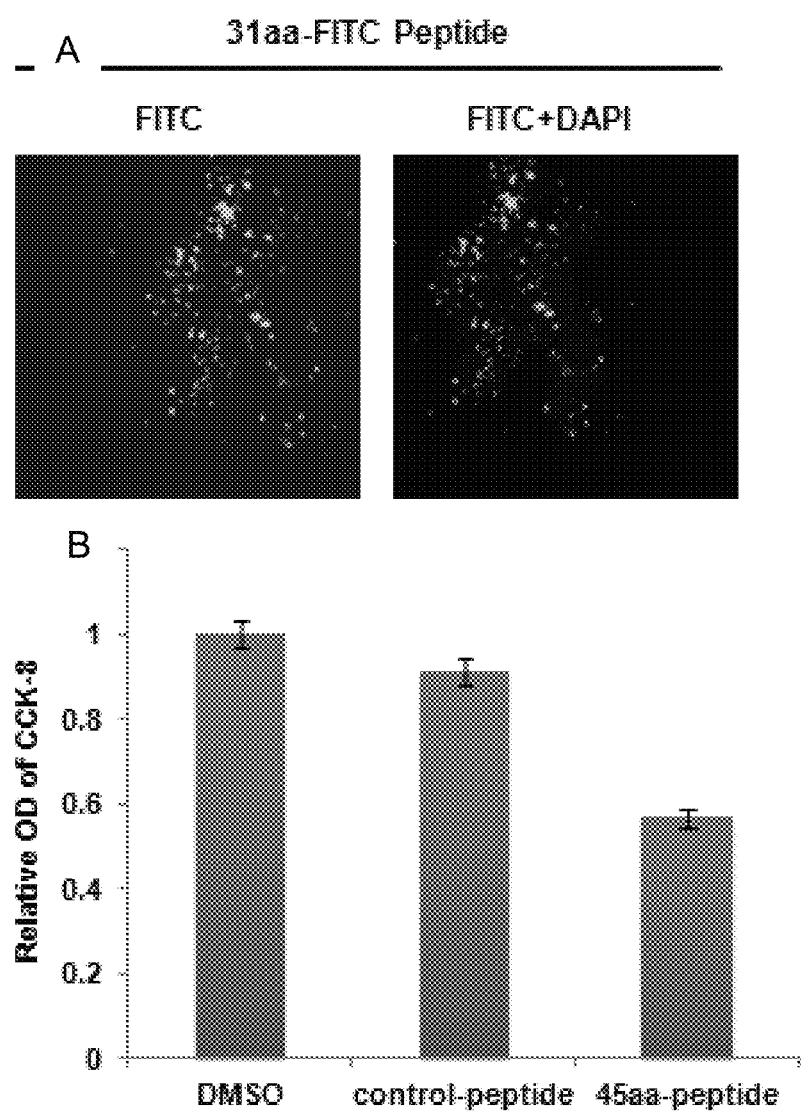
FIG. 4 illustrates that the chemically synthesized 31aa-uORF coded polypeptide can enter U251 cells and significantly suppress the growth of glioma cells;
  A: adding 31aa-peptide (concentration: 10 µM) to U251 cells, washing out of the superfluous polypeptide using PBS 4 hours later, and detection of the ability of the polypeptide to enter cells by immunofluorescence;
  B: continued cell culture for 72 hours and then detection of the cell viability with CCK-8.

In one aspect, the synthetic 31aa-uORF coded micropeptide can enter the U251 glioma cells and can significantly suppress the growth and proliferation of the U251 glioma cells (FIG. 4).

Figure 5:
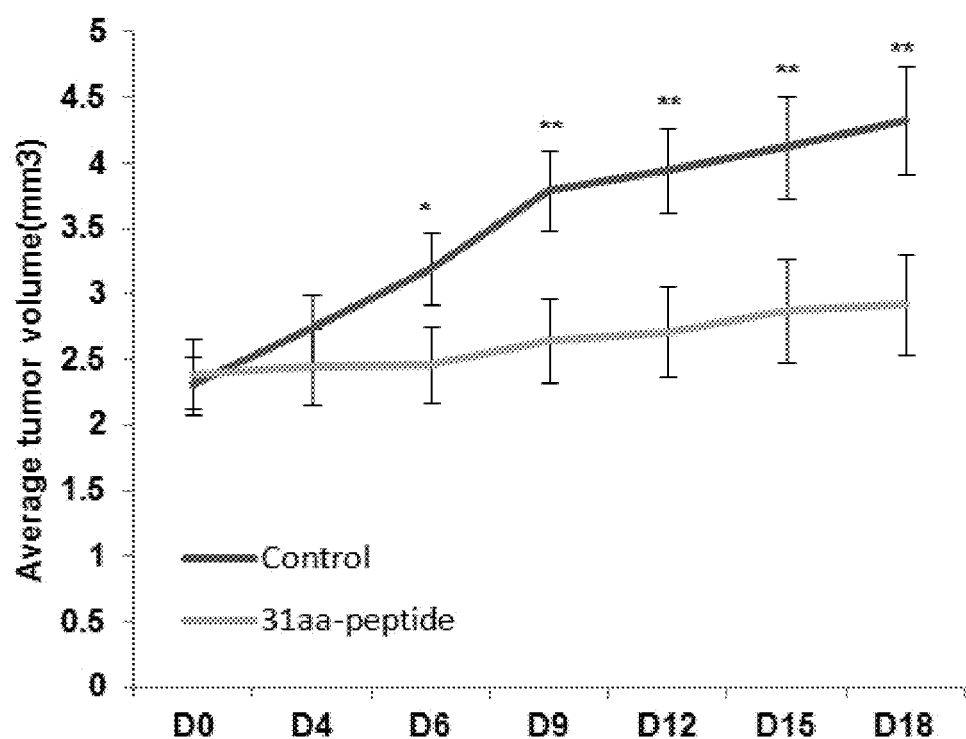
FIG. 5 illustrates that the chemically synthesized 31aa-uORF coded polypeptide can significantly suppress the growth of the U251 tumor subcutaneously implanted in nude mice.

In one aspect, the anti-tumor ability of the 31aa-uORF coded micropeptide is verified in vivo by animal experiments in the present invention. Mice are subcutaneously inoculated with 2 million U251 glioma cells. Thirty days later, transplanted tumors are treated with the chemically synthesized 31aa-uORF coded micropeptide (25 ug/tumor) every other day. It is found that compared with a control polypeptide (the control polypeptide is synthesized by randomly shuffling the sequence of the 31aa-uORF coded polypeptide), the chemically synthesized 31aa-uORF coded micropeptide can significantly suppress the growth and formation of the U251 glioma transplanted tumors, which indicating that the 31aa-uORF coded micropeptide also exhibits excellent anti-tumor activity at the animal level (FIG. 5).

In addition to the polypeptide having the amino acid sequence of SEQ ID NO: 2 as described above, other polypeptides conventionally modified by the sequence of the present invention should also be construed as having the tumor suppression function as described herein, such as an amino acid sequence that is at least 80%, at least 85%, at least 90%, at least 91%, at least 92%, at least 93%, at least 94%, at least 95%, at least 96%, at least 97%, at least 98%, or at least 99% similar with SEQ ID NO: 2. A polypeptide therapeutic agent may have a short circulation half-life period, proteolytic degradation and low solubility. In order to improve the pharmacokinetic and pharmacokinetic characteristics of biological pharmaceuticals of the present invention, such methods can be implemented: manipulating amino acid sequences to reduce or improve the immunogenicity and reduce proteolysis; fusing or coupling the peptide to immune globulins and serum proteins, such as albumin; and also incorporating biological pharmaceuticals (such as peptide of the present invention) and antibodies into drug delivery vectors for biological pharmaceuticals so as to protect and slow down in release of biological pharmaceuticals and antibodies. Furthermore, it is envisaged to couple the peptide to natural or synthetic polymers. Specifically, for coupling with the synthetic polymers, pegylation or acylation, such as N-acylation, S-acylation, amidation and the like, is also envisaged.

In some embodiments, the PTEN-31aa peptide may be conjugated to one or more high molecular weight compounds to improve its properties. For example, it may be conjugated to polyethylene glycol, albumin, dextran, polyoxyethylene, styrene-maleic acid copolymer, polyvinylpyrrolidone, hydroxypropylmethacrylamide, pyran copolymer, and the like, to improve stability against various chemical, physical or biological factors, to prolong the half-life in vivo, and/or to reduce immunogenicity.

PTEN-31aa molecules may also be prepared in the form of fusion proteins, containing a heterologous fusion sequence or partner. The fusion sequence may include, for example, an affinity tag sequence, such as a poly-histidine, myc-peptide or a FLAG tag. Such tags may be removed after isolation by methods known to one skilled in the art. As used herein, "pharmaceutical excipients or pharmaceutical carriers" include any and all solvents, dispersion mediums, coatings, antibacterial and antifungal agents, isotonic agents, absorption retardants, and the like. Uses of such mediums and reagents in pharmaceutical active substances are well known in the art. Unless any conventional medium or agent is incompatible with active components, the use thereof in therapeutic compositions can be expected. Supplementary active ingredients can also be incorporated into the compositions.

Pharmaceutical compositions containing a nucleotide sequence encoding a PTEN-31aa molecule, or containing a PTEN-31aa peptide, may contain one or more additional components such as carriers, excipients, diluents, pharmaceutically-acceptable carriers, stabilizers, buffering agents, preservatives, non-ionic detergents, antioxidants, and other additives. In certain embodiments, the additional components stabilize and extend the useable life of the composition, and/or prevent degradation, such as with stabilizers and preservatives. Other components may improve other properties such as solubility, reducing aggregation, and the like.

Preferably, the present invention provides a pharmaceutical composition comprising DMSO (dimethylsulfoxide) and polypeptide PTEN-31aa. As an embodiment, in the stock solution of the pharmaceutical composition, the concentration of polypeptide PTEN-31aa in DMSO is at least 20 ug/mL, and when the pharmaceutical composition is administered, the stock solution was diluted by solvent to the concentration of polypeptide PTEN-31aa in DMSO is at least 5 ug/mL, wherein the solvent is saline or PBS.

The pharmaceutical composition can be administered to a patient by a variety of routes such as orally, transdermally, subcutaneously, intranasally, intravenously, intramuscularly, intrathecally, topically or locally. Typically, the pharmaceutical compositions will be administered orally, parenterally, intravenously or subcutaneously. According to the administration route, the active components may need to be coated with a material to be protected against the effects of enzymes, acids and other natural conditions that may inactivate the components.

The dose of the pharmaceutical composition to be administered to the subject can be adjusted based on the need and the characteristics of the individual subject. Exemplary dose ranges are from 0.01 mg/kg to 100 mg/kg, 0.01 mg/kg to 50 mg/kg, 0.1 mg/kg to 30 mg/kg and 1 mg/kg to 30 mg/kg, per dose, or per day. In one embodiment, an effective amount of polypeptide PTEN-31aa is higher than 5 mg/kg, preferably greater than 10 mg/kg, and still preferably greater than 15 mg/kg.

Advantages of the Present Invention

1. According to the present invention, the small upstream open reading frame 31aa-uORF (31aa-uORF) is found in the 5' terminal of the PTEN for the first time, which can code a short peptide (PTEN-31aa) with 31 amino acids. By preparing the antibody against the PTEN-31aa, the 31aa-uORF can really be endogenously expressed in glioma cells and normal glial cells. At the same time, it is found, by detecting the expression quantities of various of glioma samples and normal samples, that the expression quantity of the 31aa-uORF in the glioma tissue samples is significantly reduced as compared with that in normal brain tissue.

2. More excitingly, whether in in-vitro experiments or in living animal experiments, the polypeptide (PTEN-31aa), regardless of being produced by recombinant expression or synthesized artificially, can significantly suppress the growth and proliferation of glioma cells.

3. The present invention also provides a polypeptide synthesized artificially or expressed by a recombination vector. The micropeptide is particularly low in molecular weight, thus can easily enter glioma cells and penetrate to tumor tissue, and can also well penetrate through the blood brain barrier to treat gliomas.

4. The invention can provide a new peptide drug and new ideas and strategies for tumor treatment, in particular clinical treatment or prevention of gliomas, based on the newly discovered upstream open reading frame (31aa-uORF) and the micropeptide (PTEN-31aa) coded by the same.

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

The following terms, unless otherwise indicated, shall be understood to have the following meanings:

As used herein, the term "nucleic acid" or "nucleic acid fragment" refers to a polymeric form of nucleotides of at least 10 bases in length. The term includes DNA molecules (e.g., cDNA or genomic or synthetic DNA) and RNA molecules (e.g., mRNA or synthetic RNA molecules), as well as analogs of DNA or RNA containing non-natural nucleotide analogs, non-native internucleotide bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. And, such "nucleic acid" or "nucleic acid fragment" may comprise modified nucleotides as a percentage of the total number of nucleotides present in the nucleic acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides).

The term "expression vectors" as used herein is intended to refer to a nucleic acid molecule capable of directing the expression of nucleic acid sequences to which they are operatively linked. One type of expression vectors is a "plasmid", which refers to a circular double stranded DNA loop into which additional DNA segments may be ligated. Other expression vectors include cosmids, bacterial artificial chromosomes (BAC) and yeast artificial chromosomes (YAC). Another preferred type of expression vectors is a viral vector, wherein additional DNA segments may be ligated into a viral genome that is usually modified to delete one or more viral genes. Certain vectors are capable of autonomous replication in a host cell into which they are introduced (e.g., vectors having an origin of replication which functions in the host cell). Other expression vectors can be integrated stably into the genome of a host cell upon introduction into the host cell, and are thereby replicated along with the host genome. Preferred viral vectors include retroviral and lentiviral vectors.

The term "overexpression" as used herein with reference to a nucleic acid sequence refers to a higher level of transcription and/or translation of a nucleic acid or protein product encoded by a nucleic acid sequence in a cell. Overexpression is most commonly accomplished by operative linkage of nucleic acid sequences to a strong promoter/enhancer sequence which stimulates transcription in the target host cell, or construction of lentivirus that containing the target nucleic acid sequence transfected host cell. (i.e., a constitutive "on" signal) or regulated (i.e., the "on" signal is induced or repressed by another signal or molecule within the cell).

The terms "polypeptide", "micropeptide" and "short peptide" should be construed as having the same meaning to express an amino acid fragment, encompassing both naturally-occurring and non-naturally-occurring proteins, and fragments, mutants, derivatives and analogs thereof, and may be monomeric or polymeric. The terms as used herein encompasses analogs and mimetics that mimic structural and thus biological function.

The terms "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

The terms "pharmaceutical carriers" refers to a carrier or a diluent that does not cause significant irritation to an organism and does not abrogate the biological activity and properties of the administered compound. Examples of suitable pharmaceutical carriers are well known in the art and include phosphate buffered saline solutions, water, emulsions, such as oil/water emulsions, various types of wetting agents, sterile solutions, etc. Pharmaceutical composition comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. Furthermore, it is envisaged that the pharmaceutical composition of the invention might comprise further biologically active agents, depending on the intended use of the pharmaceutical composition.

In the present invention the various nucleotide sequences and vectors of the invention are administered either alone or in any combination using standard vectors and/or gene delivery systems, and optionally together with a pharmaceutically acceptable carrier or excipient. Subsequent to administration, said polynucleotides or vectors may be stably integrated into the genome of the subject.

On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying of different kinds of diseases, which are related to PTEN regulation-related tumor.

Furthermore, it is possible to use a pharmaceutical composition of the invention which comprises polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Further methods for the delivery of nucleic acids comprise particle-mediated gene transfer as, e.g., described in Verma, Gene Ther. 15 (1998), 692-699.

Example 1 Endogenous Expression and Identification of 31aa-uORF Coded Micro-Peptide By using ORF Finder (website://www.bioinformatics.org/sms/orf find.html), a Open Reading Frame (ORF) of 96nt was found in the 5'UTR of the first intron region of PTEN mRNA (NM 000314). The ORF could code an oligopeptide of 31 amino acids and was named 31aa-uORF by us, and the oligopeptide coded by the ORF was named PTEN-31aa. With protein molecular weight prediction software (website://www.bio-soft.net/sms/prot_mw.html), the molecular weight of the oligopeptide was predicted to be about 4-SKD. A polyclonal antibody capable of specifically recognizing this micropeptide and detectable by western blot assay was designed according to the amino acid sequence of the 31aa-uORF. The specific method was as follows: by means of chemical polypeptide synthesis, one amino acid sequence segment TRLRSVLSSRKLQP (SEQ ID NO: 2, amino acid residues 18-31) of the 31aa-uORF was synthesized as an immunogen for injection into and immunization of a New Zealand white rabbit, and then a target antibody was purified to detect the 31aa-uORF coded micropeptide in cells. One segment of the 31aa-uORF was specifically knocked out from the genome using CRISPR/Cas9 to silence the expression of the 31aa-uORF micropeptide at the genomic level, thereby obtaining 31aa-uORF knocked-out 293 cell line. The endogenous expression and change of the 31aa micropeptide were detected by western with the 31aa-uORF specific antibody.

```
homo-31aa-uORF (96nt) nucleotide sequence
                                         SEQ ID NO: 1
ATGTGGCGGGACTCTTTATGCGCTGCGGCAGGATACGCGCTCGGCGCTG

GGACGCGACTGCGCTCAGTTCTCTCCTCTCGGAAGCTGCAGCCATGA (SEQ ID NO: 1)

homo-31aa-uORF coded amino acid sequence (PTEN-
31aa)
                                         SEQ ID NO: 2
MWRDSLCAAAGYALGAGTRLRSVLSSRKLQP (SEQ ID NO: 2)
```

Details of Method

1) Establishment of CRISPR/Cas9 Knockout Cell Line

A number of gRNA sequences were designed according to the sequence of the 31aa-uORF and targeted to different regions of the 31aa-uORF, respectively, and one segment of the 31aa-uORF was specifically eliminated to obtain a cell line with the 31aa-uORF being genomically knocked out.

Detailed information of the gRNA sequences are shown below:

```
31aa-SgRNA1:
                                        SEQ ID NO: 3
5'-CAACUCUCAAACUUCCAUCA-3' (SEQ ID NO: 3)

31aa-SgRNA2:
                                        SEQ ID NO: 4
5'-UCAUGGCUGCAGCUUCCGAG-3' (SEQ ID NO: 4)

31aa-SgRNA3:
                                        SEQ ID NO: 5
5'-CUCGGAAGCUGCAGCCAUGA3' (SEQ ID NO: 5).
```

(The 5'-terminal was added with g when cloning to facilitate efficient promotion of hU6 promoter.)

HEK293T cells were transiently transfected with pX330-Puro-PTEN-SgRNA plasmid, and the efficiency of transfection was detected by sequencing. The result showed that 31aa-SgRNA2 was a high efficiency SgRNA.

The 31aa-SgRNA2 plasmid was selected for the follow-up experiment and used to transfect HEK293 cells. The HEK293 cells transfected with 31aa-SgRNA2 were screened using puromycin and the positive clones were picked out. One clone cell thereof, numbered Ell, be deleted 9 bases (specific sequence thereof: GAGAGGAG), with frameshift mutation, could meet our requirements. Thus, the cell line with the 31aa-uORF being genomically knocked out was obtained.

2) Cell Culture

HEK-293T cells were purchased from ATCC (ATCC® CRL-11268™), cultured in DMEM (Gibco, 8113281) medium containing 10% Fetal Bovine Serum (FBS, Gibco, 10099) and 10 U/mL penicillin-streptomycin (Gibco, 15140-122), and placed in a constant-temperature moist incubator with 5% CO2 at 37° C. The cells were passaged every three days with a passage ratio of 1:4.

3) Western Blot

The total protein of cells was extracted with *RAPA*, and the extracted protein was quantified by BCA protein assay; 5% SDS-PAGE spacer gel and 15% SDS-PAGE separating gel were disposed, and the total protein of the loaded sample was 100 micrograms. Protein electrophoresis was run at 80V for 20 minutes and at 150V for 1 hour. Protein was transferred to a membrane at 100V for 2 hours. 5% skim milk was used for sealing for 1 hour. Rabbit anti-31aa-uORF antibody (1:500), (3-actin antibody (Abcam No. ab197345) (1:3,000) were incubated at 4 DEG C. overnight. In the next day, rabbit secondary antibody (1:10,000) was incubated at normal temperature for 1 hour; TBST was used for washing for 5 times, each for 5 minutes, and then lighting, developing and fixing were carried out.

Experimental Results:

By preparing the 31aa-uORF specific antibody, we detected and identified the real existence of the uORF coded micropeptide in the 293 and U251 cells (FIG. 2). Meanwhile, it was also found that the expression quantity of the micropeptide in normal brain glial cells was much higher than that in glioma cells, suggesting that the micropeptide might have the tumor suppression function (FIG. 2).

Example 2 Determination of Biological Functions of 31aa-uORF Micropeptide 1) Establishment of Overexpressed 31aa-uORF Stable Cell Line Overexpressing 31aa-uORF A vector for overexpressed 31aa-uORF-GFP (the skeleton of the vector is pCDH-CMV-MCS-EF1-Puro) was constructed and then used to transfect into HEK-293T cells together with lentivirus skeleton vectors PSPAX2, PMD2G in a ratio of 4:3:1 to package the lentivirus. The medium supernatants with the lentivirus were collected at 48 hours and 72 hours, respectively, and then used to infect U251 cells (added with 8 ug/ml polybrene to improve the infection efficiency). Puromycin (1 mg/mL) was employed for screening and removed three days later, and then the cells were proliferated normally. Steps of cell transfection include: inoculating 0.5 million 293T cells into a 6-well culture plate, and performing transfection after cell adherence to the wall in 24 hours; before transfection, preparing 100 µL serum-free medium DMEM and plasmid into a mixed liquid; uniformly mixing 100 µL serum-free medium DMEM with 5 µL (2 ug plasmid/5 µL lipo2000) liop2000 liposome into a liposome mixed liquid; mixing the two mixed liquids in equal proportions and standing at room temperature for 20 minutes; operating according to the operating instructions of the transfection reagent; with the final volume in the wells of the 6-well plate being 1 ml, performing transfection for 6 hours, and then replacing with 1 ml normal medium (10% fetal bovine serum added with 90% DMEM medium and 1% penicillin-streptomycin) for cell culture under the conditions of 37 DEG C. and 5% carbon dioxide.

2) Flow Cytometry in Analysis of Cell Cycle 1.5 Million U251 glioma cells of lentivirus overexpressed 31aa-uORF were inoculated into a T25 culture flask. The cells were cultured for 24 hours continuous after being adhered to the wall in DMEM (Gibco, 8113281) containing 10% fetal bovine serum (FBS, Gibco, 10099) and 10 U/mL penicillin-streptomycin (Gibco, 15140-122) and placed in a constant-temperature moist incubator with 5% CO2 at 37° C. Trypsinized cells were centrifuged and then washed with PBS once, and then centrifuged again to remove the supernatant; and the precipitate was resuspended in 1 mL PBS and then added dropwise with 3 mL 100% ethyl alcohol pre-cooled at −20 DEG C. for cell fixation for 30 minutes. Then, after being centrifuged and washed with PBS once, the precipitate was resuspended in 25 ug/mL Propidium Iodide (PI, sigma)/PBS solution, stained for 30 minutes away from light, and then detected on cell-cycle distribution thereof.

3) Detection of Cell Proliferation with CCK-8

U251-GFP control cells or U251-31aa-uORF-GFP cells were inoculated into a 96-well plate in a quantity of 2000 cells per well. Each sample was repeated 5 times. After cell adherence to the wall, the CCK-8 (Dojindo, CK04) reagent was added by 10 µL per well every 24 hours for culture at 37° C. for 1-4 hours, and then the absorbance (OD) of 450 km was detected. The absorbance value was directly proportional to the number of cells.

4) Clone Formation Assay (CFA)

U251-GFP control cells or U251-31aa-uORF-GFP cells were inoculated into a 6-well plate in a quantity of 2000 cells per well and continuously cultured in a constant-temperature moist incubator with 5% CO2 at 37° C. for two weeks. Then, a picture was taken after staining with crystal violet, and the number of the formed clones was determined. The assay was repeated at least three times.

5) Soft Agar Assay

Firstly, 2 mL 0.6% (prepared in DMEM) low-gelling temperature agarose was added to a 6-well plate, and after the agarose was coagulated, 2 mL 0.35% (prepared in DMEM) low-gelling temperature agarose containing 20000 U251-GFP control cells or U251-31aa-uORF-GFP cells was added thereto and uniformly mixed by shaking slightly for continuous culture in a constant-temperature moist incubator with 5% CO2 at 37° C. for two weeks. Then, a picture was taken under an optical microscope and the number of the formed clones was determined. The assay was repeated at least three times.

Experimental Results:

In U251 glioma cells, the overexpressed 31aa-uORF coded micropeptide could significantly suppress the growth, proliferation and clone formation of U251 glioma cells (FIG. 3).

Example 3 Verification of Ability of Micropeptide to Enter Cells

U251 cells were inoculated onto a glass slide at the density of 50%, and different concentrations of PTEN-31aa micropeptide attached with FITC fluorescent groups (the micropeptide was dissolved in DMSO with a concentration being 20 μg/μL, 5 mM) were added to treat cells for 4 hours, then fixed with Faure Marin, and observed and photographed under a fluorescence microscope. It was found that the PTEN-31aa micropeptide in the concentration of 10 μM could enter the U251 cells smoothly in 4 hours, and all cells in sight were fluorescent (FIG. 4).

Example 4 Verification of Tumor Suppression Function of 31aa-uORF Micropeptide at the Animal Level U251 cells were inoculated to the left and right sides of nude mice by 2 million at each point. Thirty days later, the formation of tumors was observed, and the tumors were averagely divided into a control group and an experimental group by size (five nude mice and ten tumors in each group). The control group was injected with a control polypeptide every other day, and the experimental group was injected with the 31aa-uORF polypeptide every other day. Each tumor was injected with 25 ug synthetic peptide. The long diameters and short diameters of the tumors were measured before the medication, and after 7 times medications, the nude mice were sacrificed, and tumors were taken out, photographed and weighed.

Tumor volume=½*long diameter*the square of short diameter

The experimental results, as shown in FIG. 5, showed that the chemically synthesized 31aa-uORF coded micropeptide could significantly suppress the growth and formation of the tumors transplanted by glioma U251 as compared with the control polypeptide (the control polypeptide was synthesized by randomly shuffling the sequence of the 31aa-uORF coded polypeptide), indicating that the 31aa-uORF coded micropeptide also exhibited excellent anti-tumor activity at the animal level.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "WANH-61860-Sequences_ST25.txt", created Dec. 5, 2019, file size of 4,096 bytes, is hereby incorporated by reference.

The invention claimed is:

1. A method for treating a glioma in a subject in need thereof, comprising administering to the subject a therapeutically effective amount of a polypeptide, wherein the polypeptide has an amino acid sequence consisting of the amino acid sequence of SEQ ID NO: 2.

2. The method of claim 1, wherein said polypeptide is administered at 0.01 mg/kg to 100 mg/kg per dose and/or per day.

3. The method of claim 2, wherein said polypeptide is conjugated to one or more high molecular weight compounds.

* * * * *

```
                       SEQUENCE LISTING

<160> NUMBER OF SEQ ID NOS: 11

<210> SEQ ID NO 1
<211> LENGTH: 96
<212> TYPE: DNA
<213> ORGANISM: Homo sapiens

<400> SEQUENCE: 1
atgtggcggg actctttatg cgctgcggca ggatacgcgc tcggcgctgg gacgcgactg      60
cgctcagttc tctcctctcg gaagctgcag ccatga                               96

<210> SEQ ID NO 2
<211> LENGTH: 31
<212> TYPE: PRT
<213> ORGANISM: Homo sapiens

<400> SEQUENCE: 2

Met Trp Arg Asp Ser Leu Cys Ala Ala Ala Gly Tyr Ala Leu Gly Ala
1               5                   10                  15

Gly Thr Arg Leu Arg Ser Val Leu Ser Ser Arg Lys Leu Gln Pro
            20                  25                  30

<210> SEQ ID NO 3
<211> LENGTH: 20
<212> TYPE: RNA
<213> ORGANISM: Artificial Sequence
<220> FEATURE:
<223> OTHER INFORMATION: Synthetic construct guide RNA sequence

<400> SEQUENCE: 3
caacucucaa acuuccauca                                                 20
```

```
<210> SEQ ID NO 4
<211> LENGTH: 20
<212> TYPE: RNA
<213> ORGANISM: Artificial Sequence
<220> FEATURE:
<223> OTHER INFORMATION: Synthetic construct guide RNA sequence

<400> SEQUENCE: 4
ucauggcugc agcuuccgag                                                      20

<210> SEQ ID NO 5
<211> LENGTH: 20
<212> TYPE: RNA
<213> ORGANISM: Artificial Sequence
<220> FEATURE:
<223> OTHER INFORMATION: Synthetic construct guide RNA sequence

<400> SEQUENCE: 5
cucggaagcu gcagccauga                                                      20

<210> SEQ ID NO 6
<211> LENGTH: 35
<212> TYPE: PRT
<213> ORGANISM: Mus musculus

<400> SEQUENCE: 6

Met Trp Arg Asp Ser Leu Cys Thr Ala Ala Gly Tyr Ala Leu Gly Arg
1               5                   10                  15

Arg Asp Ala Ala Ala Leu Ser Ser Leu Leu Ser Glu Ala Ala Ala Asn
            20                  25                  30

Met Glu Val
        35

<210> SEQ ID NO 7
<211> LENGTH: 31
<212> TYPE: PRT
<213> ORGANISM: Sus scrofa

<400> SEQUENCE: 7

Met Trp Arg Asp Ser Leu Cys Thr Ala Ala Gly Tyr Pro Phe Gly Ala
1               5                   10                  15

Gly Thr Arg Leu Arg Ser Val Leu Ser Ser Arg Lys Leu Gln Pro
            20                  25                  30

<210> SEQ ID NO 8
<211> LENGTH: 35
<212> TYPE: PRT
<213> ORGANISM: Bos taurus

<400> SEQUENCE: 8

Met Trp Arg Asp Ser Leu Cys Thr Ala Ala Gly Tyr Ala Leu Gly Arg
1               5                   10                  15

Arg Asp Ala Ala Ala Leu Arg Ser Leu Leu Ser Glu Ala Ala Ala Asn
            20                  25                  30

Met Glu Val
        35

<210> SEQ ID NO 9
<211> LENGTH: 35
<212> TYPE: PRT
<213> ORGANISM: Oryctolagus cuniculus

<400> SEQUENCE: 9
```

-continued

```
Met Trp Arg Asp Ser Leu Cys Thr Ala Ala Gly Tyr Ala Pro Gly Arg
1               5                   10                  15

Trp Asp Ala Ala Ala Leu Ser Ser Leu Leu Ser Glu Ala Ala Ala Asn
            20                  25                  30

Met Glu Val
        35

<210> SEQ ID NO 10
<211> LENGTH: 15
<212> TYPE: PRT
<213> ORGANISM: Artificial Sequence
<220> FEATURE:
<223> OTHER INFORMATION: Synthetic construct consensus sequence
<220> FEATURE:
<221> NAME/KEY: MISC_FEATURE
<222> LOCATION: (8)..(8)
<223> OTHER INFORMATION: Xaa corresponds to Ala or Thr
<220> FEATURE:
<221> NAME/KEY: MISC_FEATURE
<222> LOCATION: (13)..(13)
<223> OTHER INFORMATION: Xaa corresponds to Ala or Pro
<220> FEATURE:
<221> NAME/KEY: MISC_FEATURE
<222> LOCATION: (14)..(14)
<223> OTHER INFORMATION: Xaa corresponds to Leu, Phe, or Pro

<400> SEQUENCE: 10

Met Trp Arg Asp Ser Leu Cys Xaa Ala Ala Gly Tyr Xaa Xaa Gly
1               5                   10                  15

<210> SEQ ID NO 11
<211> LENGTH: 57
<212> TYPE: DNA
<213> ORGANISM: Artificial Sequence
<220> FEATURE:
<223> OTHER INFORMATION: Synthetic construct pSin-EF2-puro-oligo

<400> SEQUENCE: 11
aattgggatc cccggacgaa ttcttcgaac atatgaagct tgctagcact agtgatc      57
```